United States Patent
Shibasaki

(10) Patent No.: US 8,223,198 B2
(45) Date of Patent: Jul. 17, 2012

(54) ENDOSCOPE PROCESSOR AND ENDOSCOPE SYSTEM

(75) Inventor: Yuichi Shibasaki, Saitama (JP)

(73) Assignee: Hoya Corporation, Tokyo (JP)

( * ) Notice: Subject to any disclaimer, the term of this patent is extended or adjusted under 35 U.S.C. 154(b) by 595 days.

(21) Appl. No.: 12/468,291

(22) Filed: May 19, 2009

(65) Prior Publication Data

US 2009/0290017 A1 Nov. 26, 2009

(30) Foreign Application Priority Data

May 21, 2008 (JP) ................................ 2008-133527

(51) Int. Cl.
H04N 7/18 (2006.01)
(52) U.S. Cl. ........................................................ 348/65
(58) Field of Classification Search .......... 348/575–577, 348/582, 587, 592, 599, 65
See application file for complete search history.

(56) References Cited

U.S. PATENT DOCUMENTS

| | | | |
|---|---|---|---|
| 2007/0269088 A1 | 11/2007 | Ikemoto | |
| 2008/0097151 A1 | 4/2008 | Inoue et al. | |
| 2009/0122135 A1 | 5/2009 | Matsui | |
| 2009/0147077 A1 | 6/2009 | Tani et al. | |
| 2009/0147078 A1 | 6/2009 | Tani et al. | |

FOREIGN PATENT DOCUMENTS

| | | |
|---|---|---|
| JP | 2002-143079 | 5/2002 |
| JP | 2002143079 A * | 5/2002 |
| JP | 2006-192058 | 7/2006 |

OTHER PUBLICATIONS

English language Abstract of JP 2002-143079, May 21, 2002.
English language Abstract of JP 2006-192058, Jul. 27, 2006.

* cited by examiner

Primary Examiner — Moustafa M Meky
Assistant Examiner — Hee Soo Kim
(74) Attorney, Agent, or Firm — Greenblum & Bernstein, P.L.C.

(57) ABSTRACT

An endoscope processor including a receiver and a correction circuit block is provided. The receiver receives an image signal. The image signal corresponds to a captured subject. The image signal is generated by an imaging device. The image signal comprises a plurality of pixel signals corresponding to a plurality of pixels. A plurality of pixels forms an optical image of the subject. The correction circuit block carries out first signal processing on the pixel signals so that a representative value matches a standard value when the image signal received by the receiver is a fluorescence image signal. The representative value is calculated on the basis of a plurality of chrominance difference values corresponding to a plurality of pixel signals. The fluorescence image signal is generated when the subject is illuminated with excitation light. The excitation light makes an organ fluoresce.

12 Claims, 8 Drawing Sheets

ENDOSCOPE PROCESSOR AND ENDOSCOPE SYSTEM

BACKGROUND OF THE INVENTION

1. Field of the Invention

The present invention relates to an endoscope processor that generates an image, to be adequately displayed for medical examination, on the basis of an optical image of a subject illuminated by excitation light and/or reference light.

2. Description of the Related Art

An autofluorescence endo scope system which directs excitation light in order to make an organ autofluoresce and which also captures an autofluorescence image of an organ is already known. In general, diseased tissue autofluoresces less than healthy tissue. Japanese Unexamined Patent Publications Nos. 2002-143079 and 2006-192058 propose an autofluorescence endo scope system which is able to provide an image for assisting in medical examination by taking advantage of the above properties.

The color of an autofluorescence sub-image of diseased tissue is sometimes different from that of healthy tissue. In addition, the color of an autofluorescence image is mainly greenish. Accordingly, it is difficult to discriminate small differences in color between diseased and healthy tissues. The autofluorescence endoscope system proposed above is unable to display such a slight color difference clearly.

SUMMARY OF THE INVENTION

Therefore, an object of the present invention is to provide an endoscope processor that carries out signal processing to enhance the autofluorescence color contrast in an image.

According to the present invention, an endoscope processor comprising a receiver and a correction circuit block, is provided. The receiver receives an image signal. The image signal corresponds to a captured subject. The image signal is generated by an imaging device. The image signal comprises a plurality of pixel signals corresponding to a plurality of pixels. A plurality of pixels forms an optical image of the subject. The correction circuit block carries out first signal processing on the pixel signals so that a representative value matches a standard value when the image signal received by the receiver is a fluorescence image signal. The representative value is calculated on the basis of a plurality of chrominance difference values corresponding to a plurality of pixel signals. The fluorescence image signal is generated when the subject is illuminated with excitation light. The excitation light makes an organ fluoresce.

Further, the correction circuit block comprises a first generation circuit block, a first calculation circuit block, and a main correction circuit block. The first generation circuit block generates chrominance difference signal components corresponding to the chrominance difference values on the basis of the pixel signal. The first calculation circuit block calculates the representative value on the basis of the chrominance difference signal components corresponding to a plurality of the pixels of a single image signal. The main correction circuit block corrects the chrominance difference signal components of all the pixels so that the representative value matches the standard value.

Further, the endoscope comprises a second generation circuit block, a second calculation block, and a color-enhancement circuit block. The second enhancement circuit block generates luminance signal components corresponding to the pixel signals on the basis of the pixel signals. The second calculation circuit block calculates luminance differences. The luminance difference is difference between first and second luminance values for the same pixel. The first luminance value corresponds to luminance signal component on the basis of reference image signal. The reference image signal is generated when the subject is illuminated with reference light. A wavelength band of the reference light is broader than that of the excitation light. The second luminance value corresponds to luminance signal component on the basis of the fluorescence image signal. The color-enhancement circuit block generates color-enhanced pixel signals by adjusting corrected pixel signals on the basis of the luminance differences. The corrected pixel signals are the pixel signals which the correction circuit block carries out first signal processing on.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
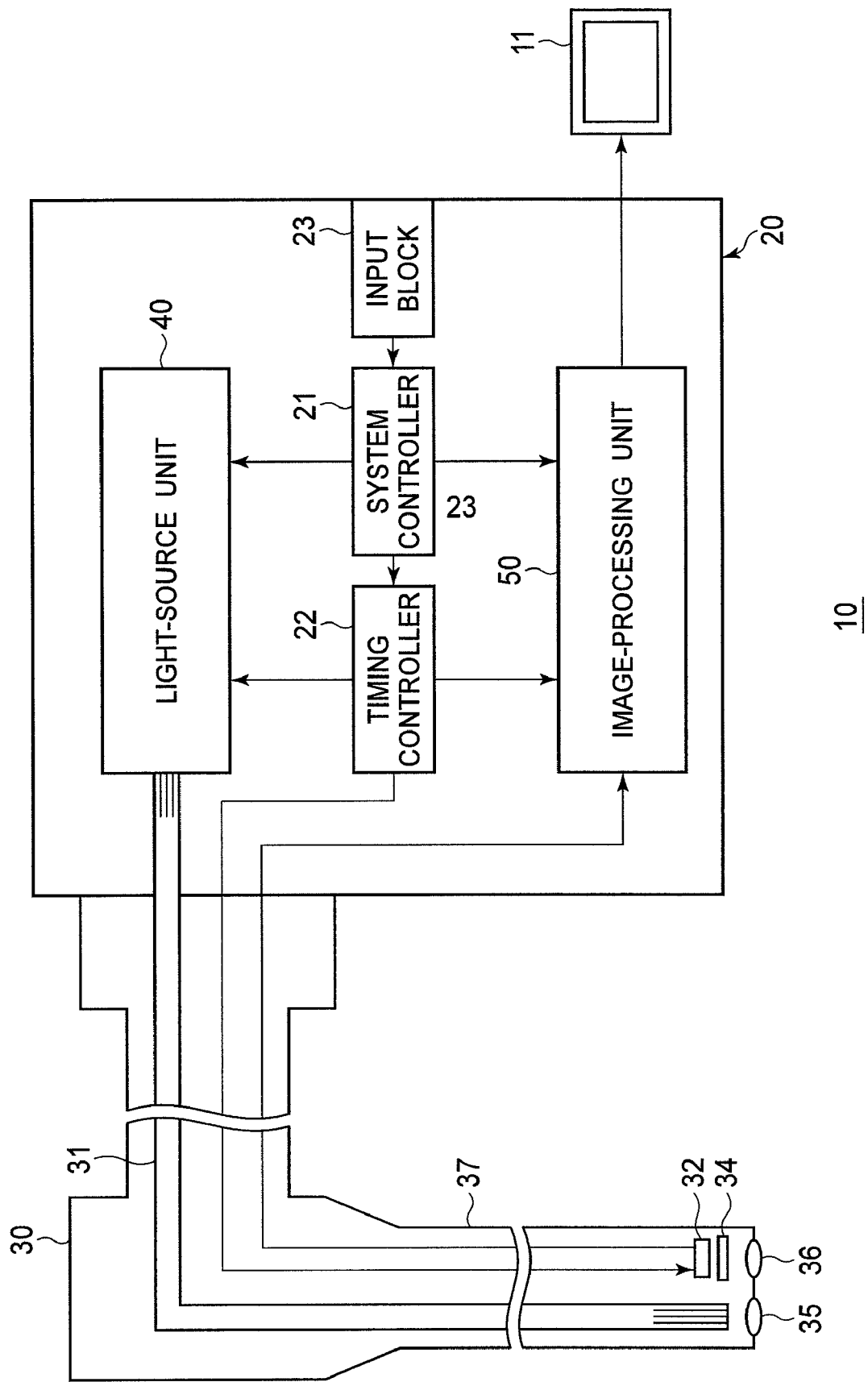
FIG. 1 is a block diagram showing the internal structure of an endoscope system having an endoscope processor of the first and second embodiments of the present invention.

The present invention is described below with reference to the embodiment shown in the drawings.

In FIG. 1, an endoscope system 10 comprises an endoscope processor 20, an electronic endoscope 30, and a monitor 11. The endoscope processor 20 is connected to the electronic endoscope 30 and the monitor 11.

The endoscope processor 20 emits light to illuminate a required subject. An optical image of the illuminated subject is captured by the electronic endoscope 30, and then the electronic endoscope 30 generates an image signal. The image signal is transmitted to the endoscope processor 20.

The endoscope processor 20 carries out predetermined signal processing on the received image signal, and then a video signal is generated. The video signal is transmitted to the monitor 11, where an image corresponding to the video signal is displayed.

The endoscope processor 20 comprises a light-source unit 40, an image-processing unit 50, a system controller 21, a timing controller 22, an input block 23, and other components. As described below, the light-source unit 40 emits white light, which illuminates a desired object, and excitation light, which makes an organ autofluoresce. In addition, as described below in detail, the image-processing unit 50 carries out predetermined signal processing on the image signal.

The system controller 21 controls the operations of all components, including the light-source unit 40 and the image-processing unit 50, of the endoscope system 10. The timing controller 22 times some operations of the components of the endoscope processor 10. The user is free to input an operational command to the input block 23, which comprises a keyboard (not depicted), a pointing device such as a mouse (not depicted), or other input devices.

By connecting the electronic endoscope 30 to the endoscope processor 20, the light-source unit 40 and a light-guide 31 mounted in the electronic endoscope 30 are optically connected. In addition, by connecting the endoscope processor 20 to the electronic endoscope 30, electrical connections are made; between the image-processing unit 50 and imaging device 32 (mounted in the electronic endoscope 30); and between the timing controller 22 and the imaging device 32.

Figure 2:
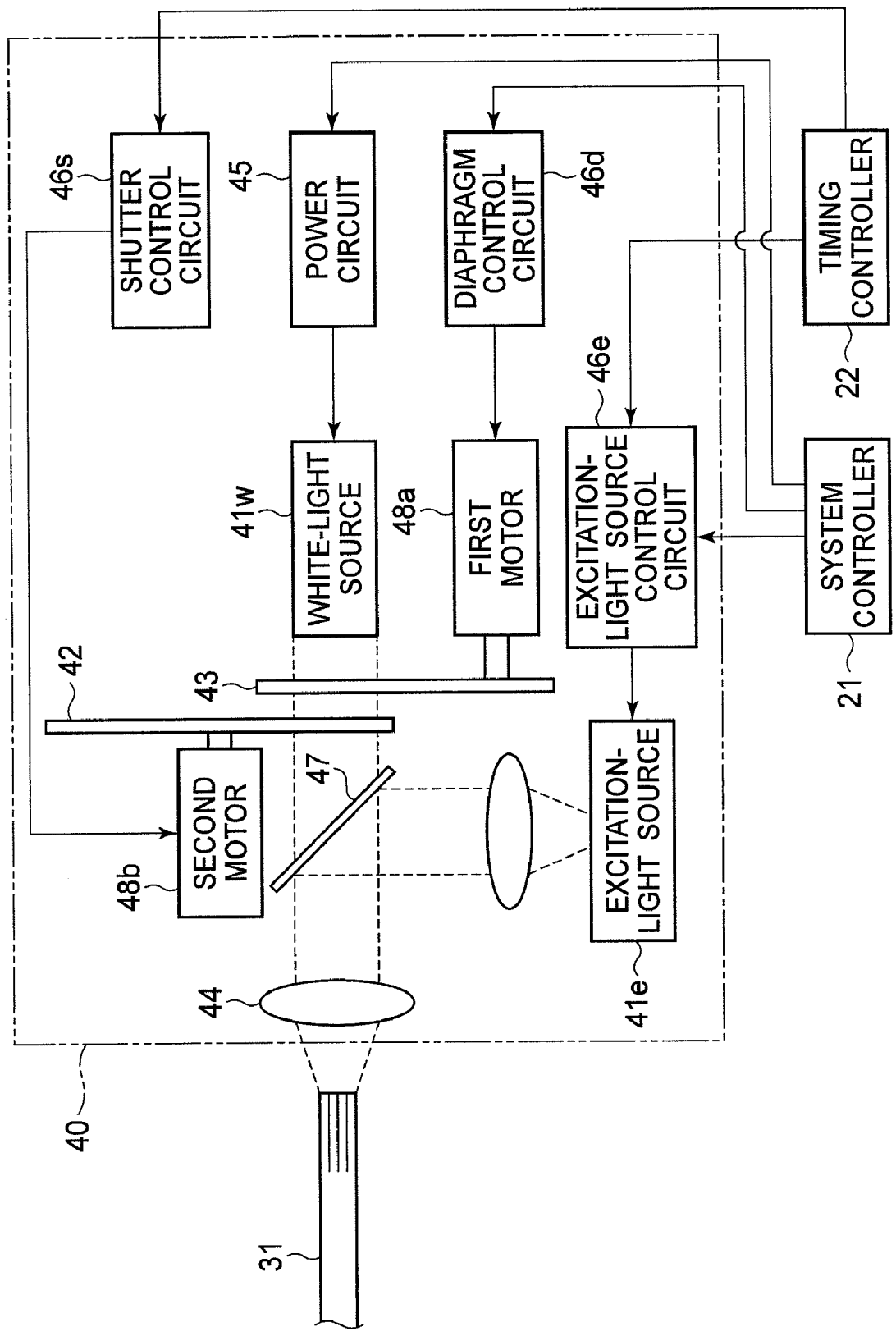
FIG. 2 is a block diagram showing the internal structure of a light-source unit.

As shown in FIG. 2, the light-source unit 40 comprises a white-light source 41$w$, an excitation-light source 41$e$, a shutter 42, a diaphragm 43, a condenser lens 44, a power circuit 45, an excitation light source control circuit 46$e$, a shutter control circuit 46$s$, a diaphragm control circuit 46$d$, and other components.

The white-light source 41$w$ emits white light. The excitation-light source 41$e$ emits exciting light of specified wavelength, such as violet light.

The diaphragm 43, the shutter 42, a dichroic mirror 47, and the condenser lens 44 are mounted between the white-light source 41$w$ and the light guide 31. The white light emitted by the white-light source 41$w$ passes the dichroic mirror 47, is condensed by the condenser lens 44, and is directed to the incident end of the light guide 31. The power circuit 45 supplies the white-light source 41$w$ with power.

The amount of the white light used to illuminate a subject, is controlled by adjusting the aperture ratio of the diaphragm 43. The aperture ratio of the diaphragm 43 is adjusted by a first motor 48$a$. The movement of the first motor 48$a$ is controlled by the diaphragm control circuit 46$d$. The diaphragm control circuit 46$d$ is connected to an image-processing unit 50 via the system controller 21.

As described below, the image-processing unit 50 detects luminance of the captured image of a subject based on the image signal generated by the imaging device. The luminance is communicated to the diaphragm control circuit 46$d$ via the system controller 21. The diaphragm control circuit 46$d$ calculates the necessary degree of adjustment for the first motor 48$a$ based on the luminance.

The shutter 42 is a rotary shutter having an aperture area (not depicted) and a blocking area (not depicted). The shutter 42 controls the passage of, or blocks the white light. When white light should be allowed to pass, the aperture area is inserted into the optical path of the white light. When white light should be blocked, the blocking area is inserted into the optical path of the white light. The shutter 42 is driven by a second motor 48$b$. The movement of the second motor 48$b$ is controlled by the shutter control circuit 46$s$.

Excitation light emitted by the excitation-light source 41$e$ is reflected by the dichroic mirror 47, condensed by the condenser lens 44, and directed to the incident end of the light guide 31. The excitation-light source control circuit 46$e$ switches the exciting-light source 41$e$ between lighting on and off.

The shutter control circuit 46$s$ and the excitation-light source control circuit 46$e$ are connected to the timing controller 22. The white-light control signal, for controlling the aperture time and blockage time of white light by shutter 42 is output from the timing controller 22 to the shutter control circuit 46$s$. In addition, the excitation-light control signal for controlling times to switch the excitation-light source 41$e$ between lighting on and off is output from the timing controller 22 to the excitation-light control circuit 46$e$. Both the white-light control signal and the exciting-light control signal are oscillating signals.

When the white-light control signal is in the high state, the shutter control circuit 46$s$ drives shutter 42 so as to pass the white light. On the other hand, when the white-light control signal is in the low state, the shutter control circuit 46$s$ drives the shutter 42 so as to block the white light.

When the excitation-light control signal is in the high state, the excitation-light control circuit 46$e$ switches the excitation-light source 41$e$ on. On the other hand, when the excitation-light control signal is in the low state, the excitation-light control circuit 46$e$ switches the excitation-light source 41$e$ off.

The timing controller 22 controls the high and low states of the white-light control signal and the excitation-light control signal so that the high and low states of the white-light control signal inverted with respect to the excitation-light control signal. Accordingly, when the white-light control signal and the excitation-light control signal are in high and low states, respectively, the white light is supplied to the incident end by the light source unit 40. On the other hand, when the white-light control signal and the excitation-light control signal are in low and high states, respectively, the excitation light is supplied to the incident end by the light source unit 40.

The endoscope system 10 has a white-light image observation mode and a first and second fluorescence image observation mode for observing a subject. When the white-light image observation mode is selected, the timing controller 22 controls the light-source unit 40 so as to continuously shine the white light on a subject. When the first fluorescence image observation mode is selected, the timing controller 22 controls the light-source unit 40 so as to continuously shine the excitation light on a subject. When the second fluorescence image observation mode is selected, the timing controller 22 controls the light-source unit 40 so as to repeatedly alternate between shining white light and excitation light.

One among the white-light image observation mode and the first and second fluorescence observation modes is selected based on an input operation to a switch (not depicted) of the endoscope 30 and the input block 23.

The power circuit 45 and the excitation-light control circuit 46$e$ are connected to the system controller 21. The system controller 21 switches the power circuit 45 and the excitation-light control circuit 46$e$ between on and off.

Next, the structure of the electronic endoscope 30 is explained in detail. As shown in FIG. 1, the electronic endoscope 30 comprises the light guide 31, the imaging device 32, an excitation-light cut off filter 34, and other components.

The incident end of the light guide 31 is mounted in a connector (not depicted) which connects the electronic endoscope 30 to the endoscope processor 20. And the other end, hereinafter referred to as the exit end, is mounted at the head end of the insertion tube 37 of the electronic endoscope 30. As described above, the white light or the excitation light emitted by the light-source unit 40 arrives at the incident end of the light guide 31. The light is then transmitted to the exit end. The light transmitted to the exit end illuminates a peripheral area near the head end of the insertion tube 37 through a diffuser lens 35.

At the head end of the insertion tube 37, an object lens 36, the excitation-light cut-off filter 34, and the imaging device 32 are also mounted. The excitation-light cut-off filter 34 is arranged between the object lens 36 and the imaging device 32.

An optical image of the subject illuminated by the white light or the exciting light is formed on a light-receiving surface of the imaging device 32 through the object lens 36 and the excitation-light cut-off filter 34.

The excitation-light cut-off filter 34 cuts off the whole band of the excitation light emitted by the excitation-light source 41e. Accordingly, the same light component as the excitation light emitted by the excitation-light source 41e from an optical image of the subject illuminated by the white light or the excitation light is attenuated by the excitation-light cut-off filter 34. The optical image passing through the excitation-light cut-off filter 34 is formed on the light-receiving surface of the imaging device 32.

The imaging device 32 is driven such that the imaging device 32 captures the optical image formed on the light-receiving surface in every field period. Field periods are usually 1/60 second in duration. The timing of various operations for driving the imaging device 32 is controlled by the timing controller 22. In addition, in the second fluorescence image observation mode, the white light and the excitation light are alternately switched to illuminate the subject in synchrony with the capture of the imaging device 32, in every field period.

The imaging device 32 generates an image signal based on the optical image captured by the light-receiving surface. The generated image signal is transmitted to the image-processing unit 50 every field period.

The imaging device 32 comprises a plurality of pixels (not depicted) on the light-receiving surface. Each pixel generates a pixel signal concordant with the level of light it receives. The image signal, thus, consists of a plurality of pixel signals which correspond to the pixels arranged on the light-receiving surface.

Each of the pixels is covered with one of red, green, and blue color filters arranged according to the Bayer arrangement. The pixel signal levels correspond to the amount of light component passing through the color filter covering them. Therefore, the pixel signal from each pixel is one of red, green, and blue signal components.

Figure 3:
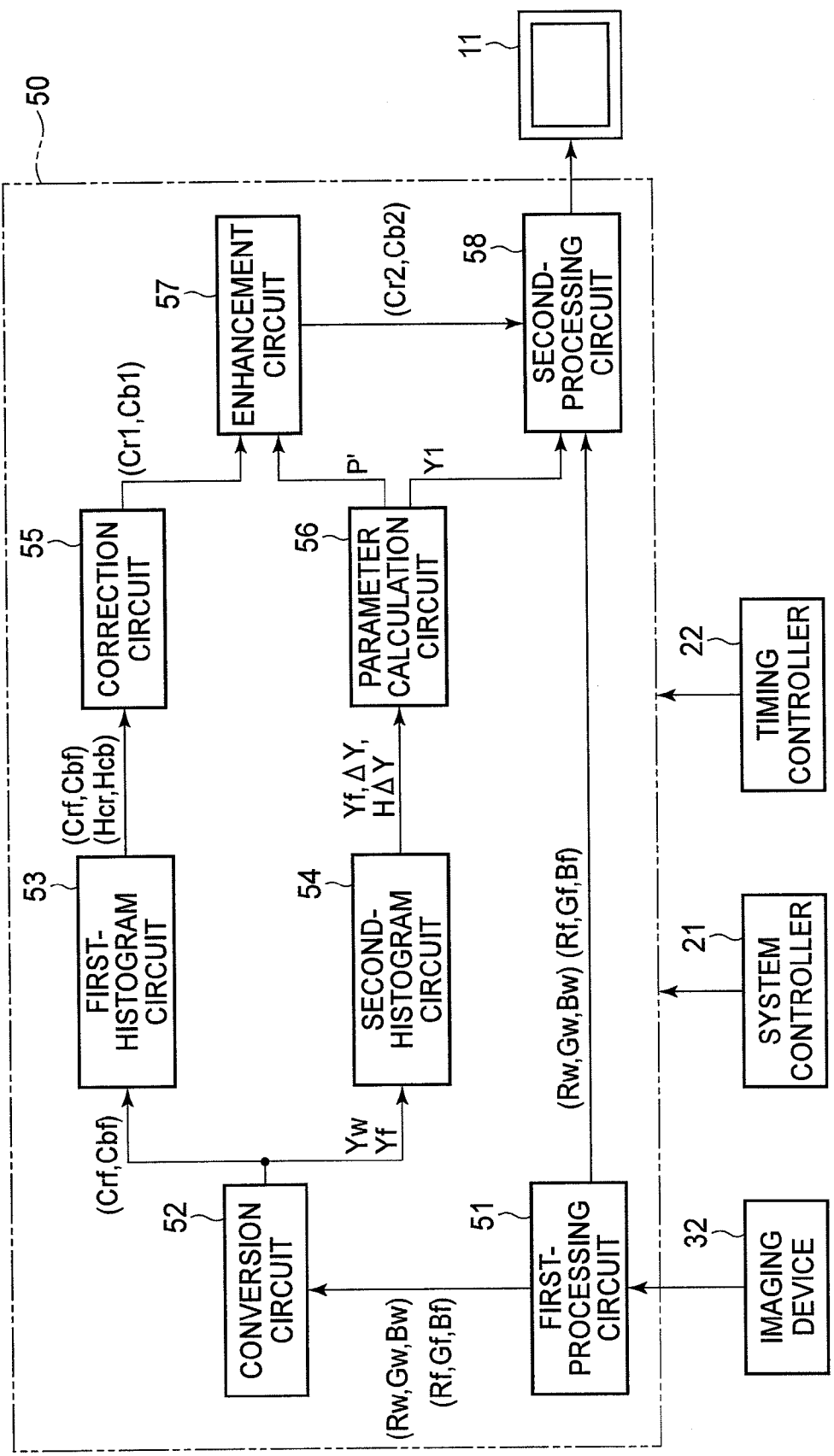
FIG. 3 is a block diagram showing the internal structure of an image-processing unit of the first embodiment.

Next, the structure of the image-processing unit 50 is explained using FIG. 3. The image-processing unit 50 comprises a first-processing circuit 51 (receiver), a conversion circuit 52 (first and second generation circuit blocks), first and second histogram circuits 53 and 54 (first and second calculation circuit block, respectively), a correction circuit 55, a parameter calculation circuit 56, an enhancement circuit 57 (color-enhancement circuit block), and a second-processing circuit 58, and other circuit components. The image-processing unit 50 is connected to a RAM (not depicted) used as working memory. As explained below, the RAM is used for the data processing carried out by each of the circuits.

The image-processing unit 50 is connected to the timing controller 22. The white- and excitation-light control signals are transmitted from the timing controller 22 to the image-processing unit 50. The image-processing unit 50 recognizes the image signal which is received while the white-light control signal is in its high state as a white light image signal. In addition, the image-signal processing unit 50 recognizes the image signal which is received while the excitation-light control signal is in its high state as a fluorescence image signal.

The white-light and fluorescence image signals received by the image-processing unit 50 are input to the first-processing circuit 51. The first-processing circuit 51 digitizes the analog image signal for conversion to image data. In addition, the first-processing circuit 51 carries out predetermined signal processing, such as gain control processing and color interpolation processing, on the image data. In gain control processing, the image data is amplified by an adjusted gain so that the median of luminance data component of the image data is matched with the median data level, as calculated by the image-processing unit 50. By color interpolation processing, other color pixel data components are interpolated for each pixel.

The first-processing circuit 51 detects the average luminance data component of the white-light image data on the basis of the white-light image data available prior to gain control processing. As described above, the detected average luminance data component is communicated to the diaphragm control circuit 46d via the system controller 21, and used for the calculation of the aperture ratio of the diaphragm 43.

When the white-light or first fluorescence image observation mode is selected, the white-light image data or the fluorescence image data continuously input to the first-processing circuit 51 is transmitted to the second-processing circuit 58. The white-light image data consists of red, green, and blue data components for a white image, hereinafter referred to as Rw, Gw, and Bw. The fluorescence image data consists of red, green, and blue data components for a fluorescence image, hereinafter referred to as Rf, Gf, and Bf.

The second-processing circuit 58 carries out predetermined data processing, such as clamp processing and blanking processing, on the image data. In addition, the second-processing circuit 58 carries out D/A conversion, and then the image data is converted to an analog image signal. Furthermore, the second-processing circuit 58 generates a video signal on the basis of the image signal and transmits the resulting video signal to the monitor 11. An image corresponding to the received video signal is thus displayed on the monitor 11. Accordingly, white-light and fluorescence images are respectively displayed when their corresponding white light and excitation light are shone.

When the second fluorescence image observation mode is selected, the white-light and fluorescence image data alternately and repeatedly input to the first-processing circuit 51 are transmitted to the conversion circuit 52.

The conversion circuit 52 generates a luminance data component, hereinafter referred to as Y, as well as chrominance difference data components for red and blue, hereinafter referred to as Cr and Cb, for each pixel, using a predetermined matrix for the Rw, Gw, and Bw, or the Rf, Gf, an Bf.

The Y, Cr, and Cb for the white-light image data (hereinafter referred to as Yw, Crw, and Cbw), are generated on the basis of the Rw, Gw, and Bw. Similarly, the Y, Cr, and Cb for the fluorescence image data, (hereinafter referred to as Yf, Crf, and Cbf), are generated on the basis of the Rf, Gf, and Bf.

Thereafter, the Crw and Cbw are deleted. However, the Crf and Cbf are transmitted to the first-histogram circuit 53. The first-histogram circuit 53 generates histograms for the Crf and Cbf for the pixel data for one field of image data.

The histogram data for the Crf and Cbf, (hereinafter referred to as Hcr and Hcb), corresponding to the generated histogram for the Crf and Cbf are transmitted to the correction circuit 55 together with the Crf and Cbf, respectively. The correction circuit 55 corrects the Crf and Cbf on the basis of the Hcr and Hcb, then corrected chrominance difference data components for red and blue, hereinafter referred to as Cr1 and Cb1, are generated. The correction carried out by the correction circuit 55 is explained in detail below.

Figure 4:
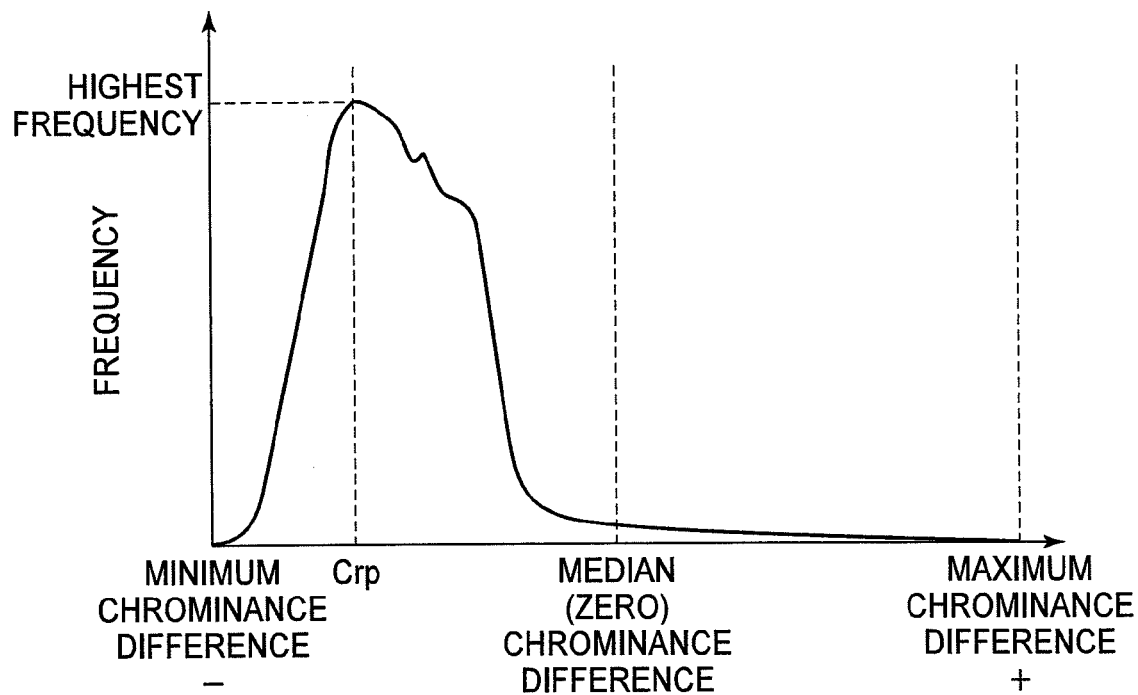
FIG. 4 is a histogram of the Crf.

The autofluorescence of an organ is mainly green. Accordingly, as shown in FIG. 4, in a sample of the frequency distribution of the Crf, the Crf frequency in the negative range is relatively great. On the basis of the Hcr, the Crf of maximal frequency (representative value) may be detected (see "Crp").

Figure 5:
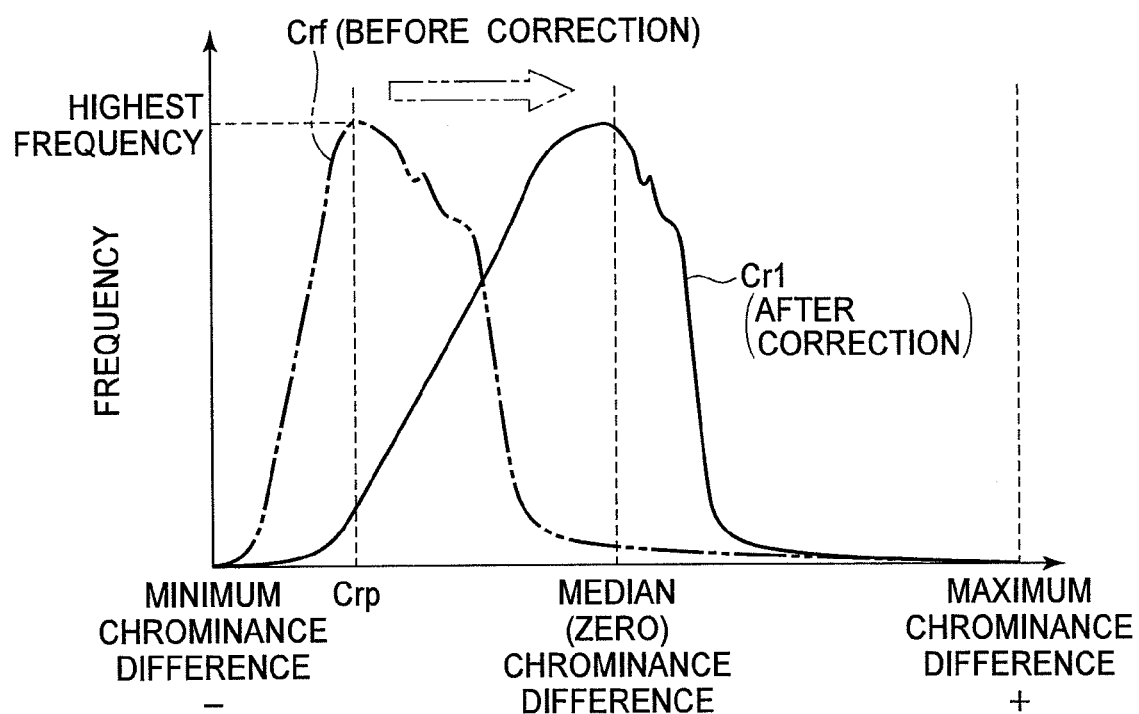
FIG. 5 is a histogram of the Cr1.

After detecting the Crf of maximal frequency (i.e., Crp), the Cr1 is generated by correcting the Crf so that the chrominance difference of the maximal frequency in the frequency distribution of the Cr1 equals zero, and thereby one whose chrominance difference is equivalent to an achromatic color (see FIG. 5). By the same processing as the Cr1, the Cbf is corrected and the Cb1 is generated.

Figure 6:
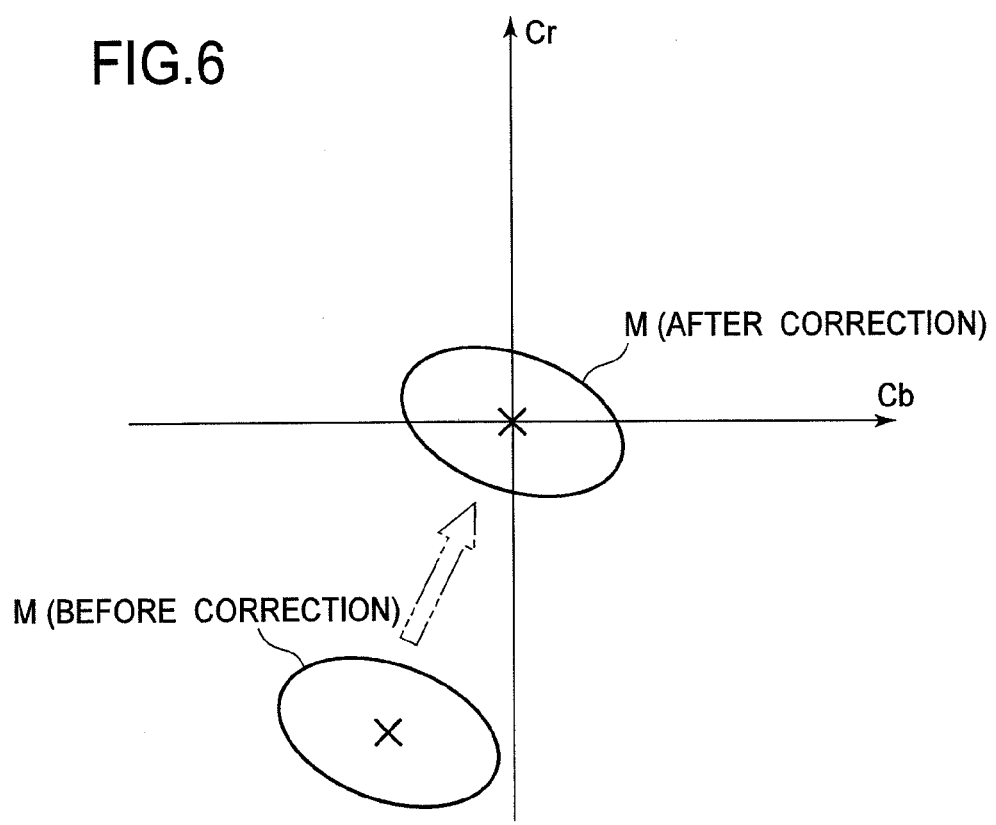
FIG. 6 is a graph of the Cr-Cb color space, used here to conceptually explain that the image of a hue to be displayed has, in fact, been corrected.

In the color space graph shown in FIG. 6, the major area (see "M") is an area where chrominance values (differences) for the Crf and Cbf are selected, descending from the highest frequency, until the cumulative sum of these frequencies reaches 80% in a given histogram of chrominance differences. In the color space graph of FIG. 6, a major area can be found in the third quadrant. The third quadrant is equivalent to green. On the other hand, once corrected, the major area for the Cr1 and Cb1 is shifted to the origin of the coordinate axis, where the color is achromatic. Through this shift, the color of a suspect tissue which is indistinguishable from the surrounding tissue in an image generated using the Crf and Cbf, becomes distinctly different from the surrounding tissue in an image generated using the Cr1 and Cb1.

Figure 7:
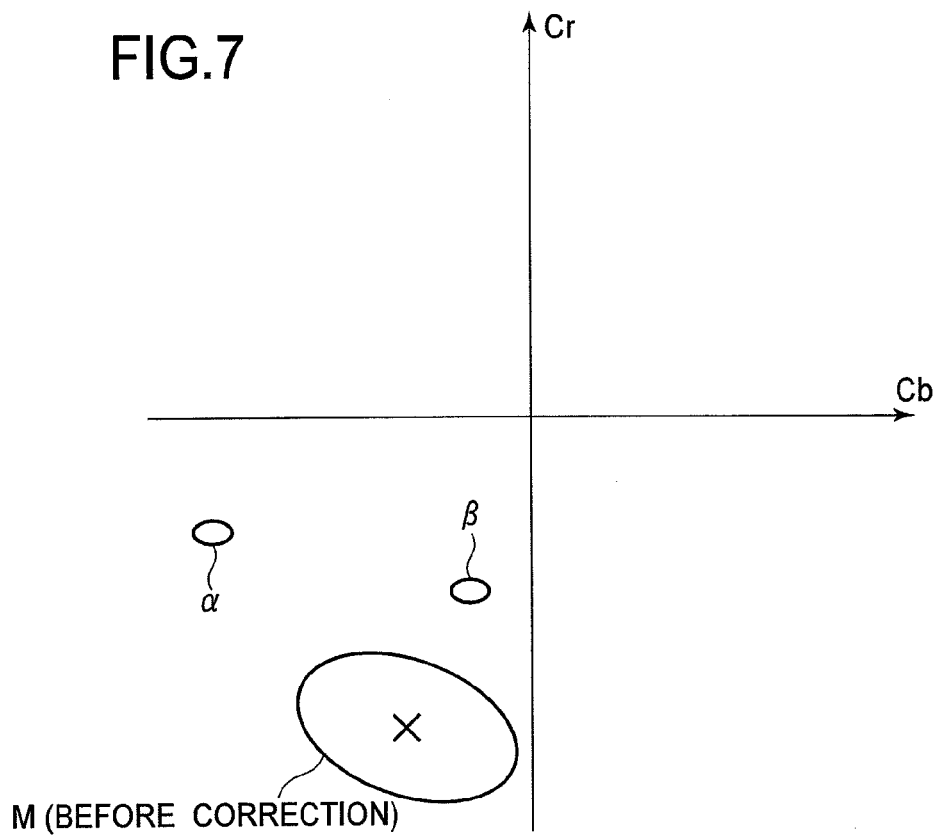
FIG. 7 is a graph of Cr-Cb color space illustrating the distribution of chrominance differences before correction, in order to conceptually explain the effect of the correction (of chrominance difference data components)

For example, in the color space graph shown in FIG. 7, even if the chrominance difference coordinates of the suspect tissue are separate from the major area (i.e., M) the color of the suspect tissue, represented by first and second areas (i.e. "α" and "β"), may have coordinates in the third quadrant (just as the major area). And in that case, the color of the suspect tissue will be indistinguishable from that of surrounding tissue in the overall image.

Figure 8:
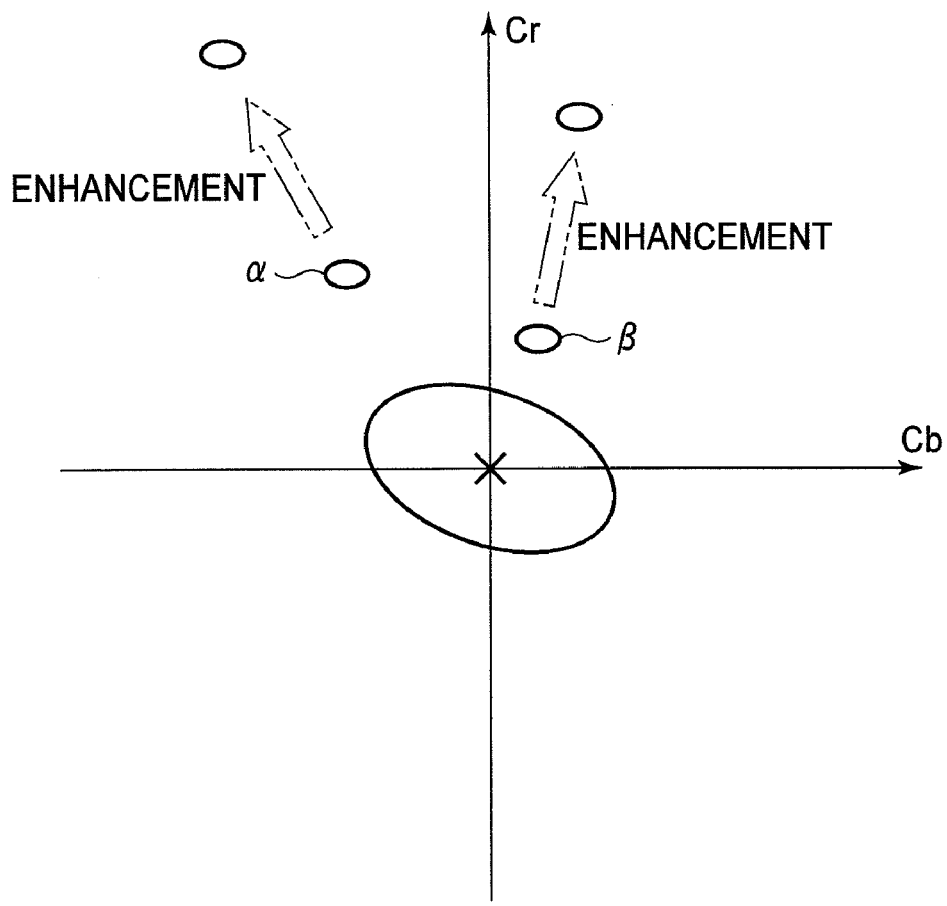
FIG. 8 is a graph of Cr-Cb color space illustrating the distribution of chrominance differences after correction, in order to conceptually explain the effect of the correction (of the chrominance difference data components)

On the other hand, in the color space graph shown in FIG. 8, by correction of the correction circuit 55, the first and second areas are shifted to the second and third quadrants, which are equivalent to red and red-violet, respectively. Accordingly, as a result of correction, the color of the suspect tissue (whose coordinates are in the first and second areas before correction), is clearly distinguishable from the color of other tissue whose coordinates are in the major area. The generated Cr1 and Cb1 are transmitted to the enhancement circuit 57. Data processing carried out by the enhancement circuit 57 is explained later.

The Yw and Yf generated by the conversion circuit 52 are transmitted to the second-histogram circuit 54. The second-histogram circuit 54 calculates luminance differences, hereinafter referred to as $\Delta Y$, which is the difference between the Yw and Yf for the same pixel. In addition, the second-histogram circuit 54 generates the histogram of the $\Delta Y$ of the pixel data of a single focused pixel and eight pixels surrounding the focused pixel, hereinafter referred to as surrounding pixels. All pixels are selected one at a time to be the focused pixel, and the histogram of the $\Delta Y$ corresponding to each pixel is generated. In addition, the number of surrounding pixels can be changed by inputting a command to the input block 23.

The generated histogram of $\Delta Y$ is transmitted as histogram data for $\Delta Y$, hereinafter referred to as H$\Delta Y$, to the parameter calculation circuit 56 with the Yf and the $\Delta Y$. The parameter calculation circuit 56 calculates an enhancement parameter on the basis of the $\Delta Y$ of each pixel. The enhancement parameter is multiplied by the Cr1 and Cb1 in order to enhance hue.

Figure 9:
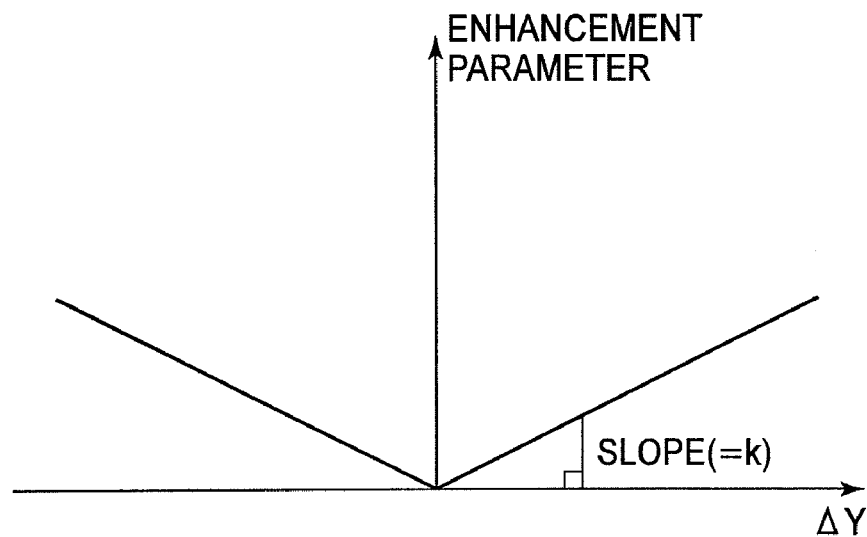
FIG. 9 is a graph showing a relationship between the enhancement parameter and luminance difference.

The enhancement parameter is calculated by a function in which the enhancement parameter increases in proportion as the absolute value of the $\Delta Y$ increases. For example, as shown in FIG. 9, the enhancement parameter is calculated by multiplying the $\Delta Y$ by a coefficient (k). In addition, the coefficient (k) can be changed to another value greater than one by inputting a command to the input block 23. Instead of calculating the enhancement parameter, the enhancement parameter may be detected according to the input $\Delta Y$ from a table containing correspondences between the enhancement parameters and the $\Delta Y$s stored in a memory.

In addition, the parameter calculation circuit 56 makes fine adjustment to the calculated enhancement parameter on the basis of the H$\Delta Y$. For fine adjustment, either ascending or descending $\Delta Y$ orders of the focused pixels are taken for the nine $\Delta Y$s of the nine pixels including a given focused pixel and its eight surrounding pixels, on the basis of the H$\Delta Y$.

The enhancement parameter is multiplied by a fine-adjustment correction value determined according to the detected order of the $\Delta Y$ of the focused pixel. Then, a finely adjusted enhancement parameter is calculated. The fine-adjustment correction value is set to a maximum of 1 when it ranks at the middle of the group of pixels in the H$\Delta Y$. In this case, when the order is fifth, the fine-adjustment correction value is set to 1. The fine-adjustment correction value is lowered as the detected order is apart from the middle order. For example, the fine-adjustment correction value is set to 0.6, 0.7, 0.8, and 0.9 when the orders are first or ninth, second or eighth, third or seventh, and fourth or sixth, respectively.

The finely adjusted enhancement parameter data (see "P'") is communicated from the parameter calculation circuit 56 to the enhancement circuit 57. In addition, the Yf is transmitted from the parameter calculation circuit 56 to the second-processing circuit 58.

As described above, the enhancement circuit 57 receives the Cr1 and Cb1 in addition to the finely adjusted enhancement parameter. The enhancement circuit 57 multiplies the Cr1 and Cb1 by the finely adjusted enhancement parameter, then enhanced chrominance difference data components for red and blue, hereinafter referred to as Cr2 and Cb2, are generated, respectively. The generated Cr2 and Cb2 are transmitted to the second-processing circuit 58.

As described above, the second-processing circuit 58 receives the Yf, the Cr2, and the Cb2. The second-processing circuit 58 carries out predetermined data processing and D/A conversion on the image data based on the Yf, the Cr2, and the Cb2. Then, the image data is converted to an image signal. Furthermore, the second-processing circuit 58 generates a video signal on the basis of the image signal and transmits the video signal to the monitor 11. An image corresponding to the received video signal is displayed on the monitor 11.

In an image displayed in the second fluorescence image observation mode, a part of a subject which autofluoresces according to different emission pattern from surrounding parts is colored with a color clearly different from that at the surrounding parts, owing to the correction of the Crf and Cbf.

In addition, the Cr1 and Cb1 are multiplied by the finely adjusted enhancement parameter, which increases in proportion to the absolute value of $\Delta Y$. Then, as shown in FIG. 8, the first and second areas (see "α" and "β"), having been shifted by the correction, are further separated from the origin of the coordinate. Accordingly, color saturation will be increased in proportion to the absolute value of $\Delta Y$. And the visible difference between parts where absolute values of $\Delta Y$ are greater than those of surrounding parts becomes even clearer.

In addition, the enhancement parameter is finely adjusted using the fine-adjustment correction value. By the fine adjustment, even though the ΔY is influenced by noise, the enhanced parameter is finely adjusted so as to be less than the originally determined one if the ΔY of the focused pixel is greatly different from that of the surrounding pixels. Accordingly, the influence of noise is reduced owing to the fine adjustment of the enhancement parameter.

Figure 10:
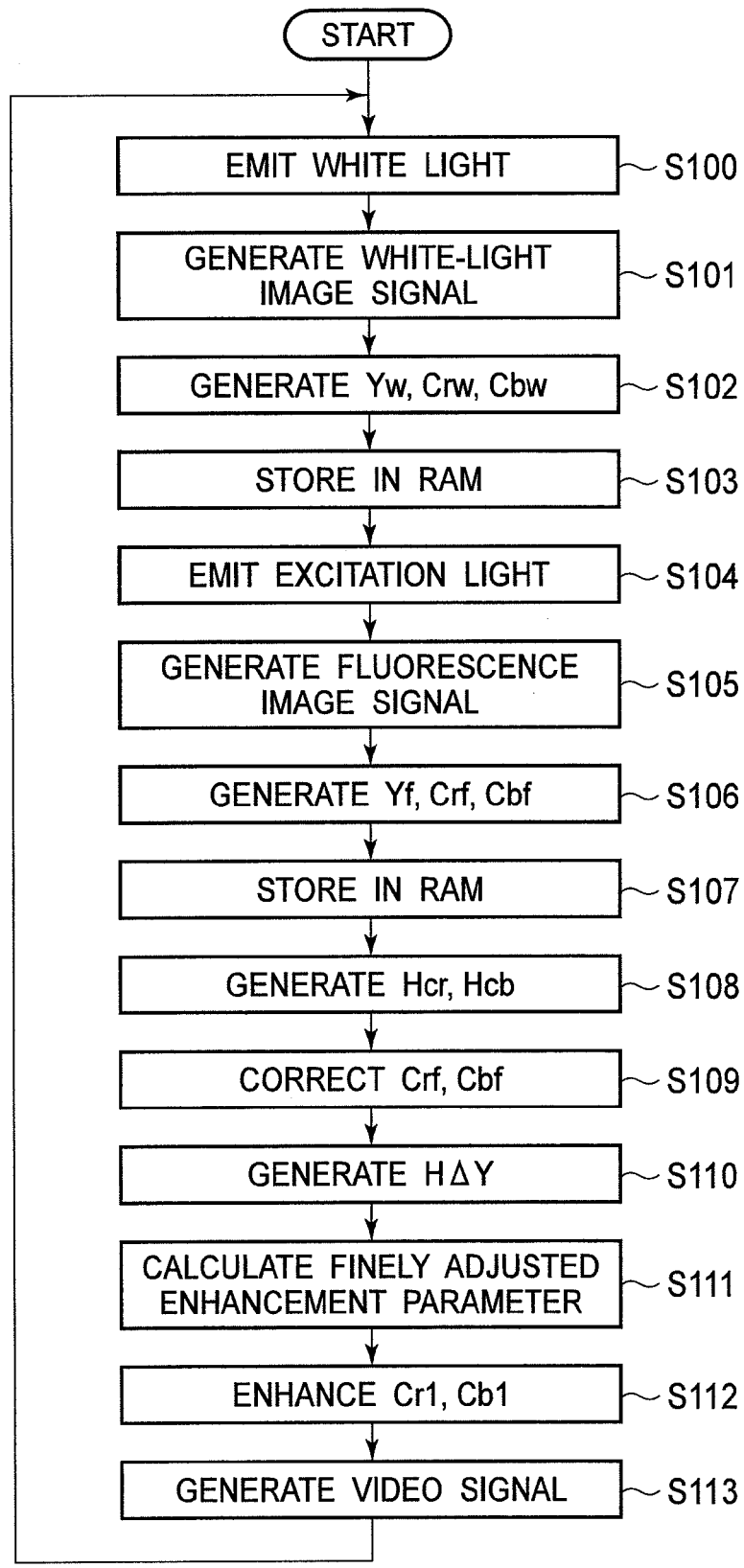
FIG. 10 is a flowchart illustrating the operations involved in generating a video signal in the second fluorescence image observation mode.

Next, operations carried out by the system controller 21 for generating a video signal in the second fluorescence image observation mode are explained below using the flowchart of FIG. 10. The operations for generating the video signal in the second fluorescence image observation mode begin when an operation mode of the endoscope system 10 is changed to the second fluorescence image observation mode. In addition, the operations finish when an operation mode is changed to another mode.

At step S100, the system controller 21 orders the light-source unit 40 to emit white light. At step S101 following step S100, the system controller 21 orders the imaging device 32 to capture an optical image of a subject illuminated by the white light and to generate a white-light image signal. After generating the white-light image signal, the process proceeds to step S102.

At step S102, the system controller 21 orders the image-processing unit 50 to generate the Yw, the Crw, and the Cbw, on the basis of the Rw, the Gw, and the Bw of the generated white-light image signal. At step S103 following step S102, the system controller 21 orders the image-processing unit 50 to store the Yw, the Crw, and the Cbw in the RAM.

At step S104 following step S103, the system controller 21 orders the light-source unit 40 to emit the excitation light. At step S105 following step S104, the system controller 21 orders the imaging device 32 to capture an optical image of a subject illuminated by the excitation light and to generate a fluorescence image signal. After generating the fluorescence image signal, the process proceeds to step S106.

At step S106, the system controller 21 orders the image-processing unit 50 to generate the Yf, the Crf, and the Cbf on the basis of the Rf, the Gf, and the Bf of the generated fluorescence image signal. At step S107 following step S106, the system controller 21 orders the image-processing unit 50 to store the Yf, the Crf, and the Cbf in the RAM. After storing, the process proceeds to step S108.

At step S108, the system controller 21 orders the image-processing unit 50 to generate the Hcr and the Hcb on the basis of the Crf and the Cbf stored in the RAM. At step S109, the system controller 21 orders the image-processing unit 50 to generate the Cr1 and the Cb1 by correcting the Crf and the Cbf on the basis of the Hcr and the Hcb. After correction of the Crf and the Cbf, the process proceeds to step S110.

At step S110, the system controller 21 orders the image-processing unit 50 to calculate the ΔY. In addition, the system controller 21 orders the image-processing unit 50 to generate the HΔY on the calculated ΔY. After generating the HΔY, the process proceeds to step S111.

At step S111, the system controller 21 orders the image-processing unit 50 to calculate the finely adjusted enhancement parameter on the basis of the ΔY and the HΔY calculated at step S110. At step S112 following step S111, the system controller 21 orders the image-processing unit 50 to calculate the Cr2 and the Cb2 by multiplying the Cr1 and the Cb1 by the finely adjusted enhancement parameter.

At step S113 following step S112, the system controller 21 orders the image-processing unit 50 to generate a video signal using the Yf stored in the RAM at step S107 and the Cr2 and the Cb2 generated at step S112. After generating the video signal, the process returns to step S100. In the above first embodiment, it is possible to generate an image in which a part of a subject, which autofluoresces following a different emission pattern from surrounding parts, or where the luminance value is lower than that of healthy tissue, is colored so that the part is distinguishable from other surrounding parts.

Next, an endoscope system having an endoscope processor of the second embodiment is explained. The primary differences between the second embodiment and the first embodiment are the method of reducing the influence of noise. The second embodiment is explained mainly with reference to the structures and functions that differ between the two embodiments. Identical index numbers are used for structures that correspond between the two embodiments.

All components except for the image-processing unit in the endoscope processor 20 of the second embodiment are the same as those of the first embodiment.

Figure 11:
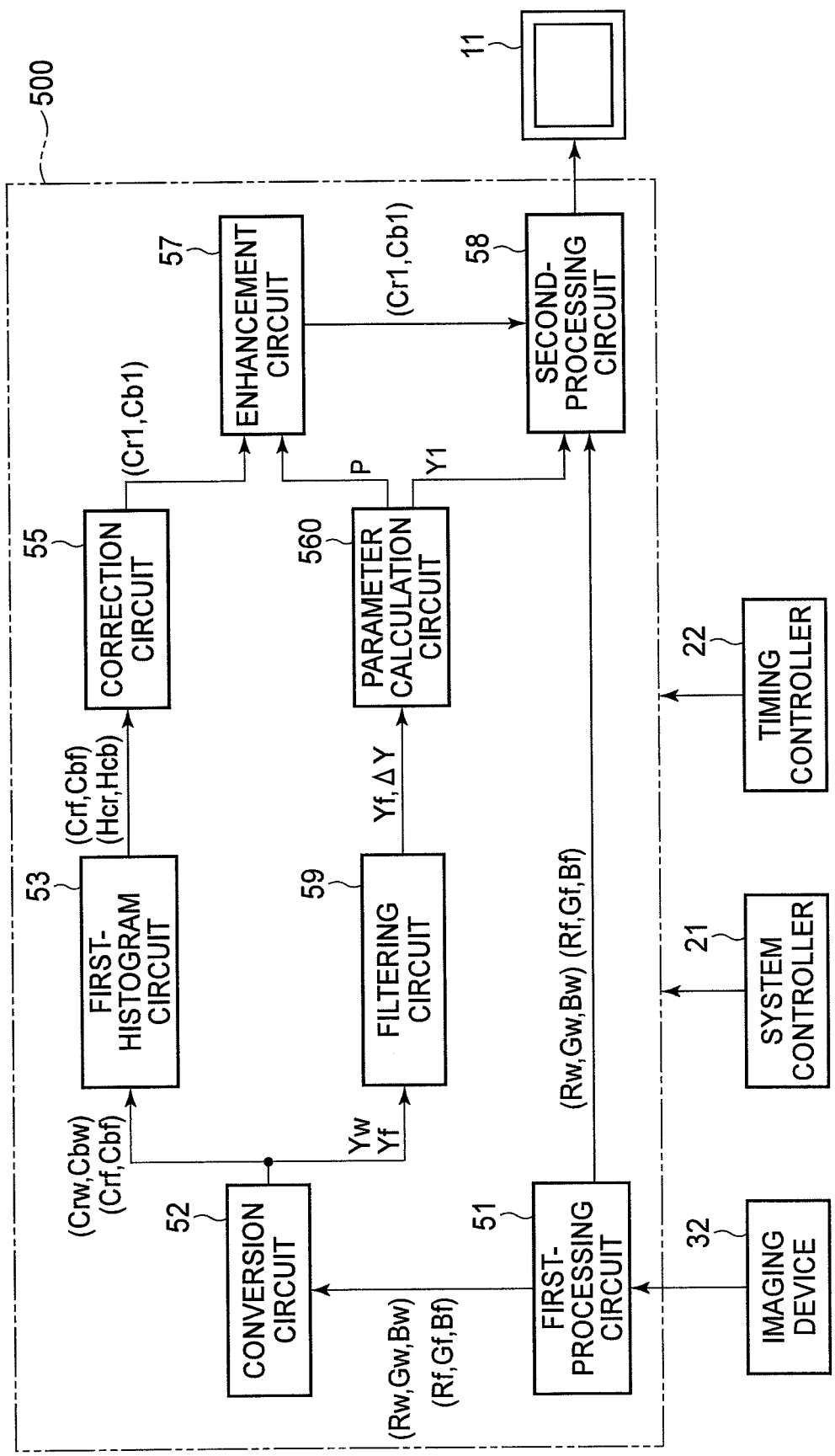
FIG. 11 is a block diagram showing the internal structure of an image-processing unit of second embodiment.

As shown in FIG. 11, an image-processing unit 500 comprises a first-processing circuit 51, a conversion circuit 52, a first histogram circuit 53, a correction circuit 55, a parameter calculation circuit 56, an enhancement circuit 57, and a second-processing circuit 58, as in the first embodiment. In addition, the image-processing unit 500 comprises a filtering circuit 59, as opposed to the first embodiment.

The functions of the first-processing circuit 51, the conversion circuit 52, the first histogram circuit 53, the correction circuit 55, the enhancement circuit 57, and the second-processing circuit 58 are the same as those of the first embodiment.

The Yw and the Yf generated by the conversion circuit 52 is transmitted to the filtering circuit 59. The filtering circuit 59 calculates ΔY on the basis of the Yw and the Yf. In addition, the filtering circuit 59 carries out laplacian filtering processing or median filtering processing on the ΔY of a selected pixel as the focused pixel, using the ΔYs of the eight surrounding pixels around the focused pixel.

The ΔY, having undergone filtering processing, is communicated with the Yf to the parameter calculation circuit 560. The parameter calculation circuit 560 calculates an enhancement parameter, as in the first embodiment. However, the parameter calculation circuit 560 communicates the enhancement parameter to the enhancement circuit 57 without fine adjustment, as opposed to the first embodiment.

In the above second embodiment, the same effect as the first embodiment can be achieved. An influence of noise on the ΔY is reduced by the filtering in the second embodiment, while the influence of noise is reduced using the histogram of ΔY in the first embodiment.

The Cr1 and the Cb1 are enhanced so that the difference (adjusted difference) between data levels of the Cr2 and the Cb2 of each pixel, and zero, (a standard data level), is increased in proportion to the absolute value of ΔY of each pixel, in the first and second embodiments. However, the Cr1 and the Cb1 can be enhanced according to any other method on the basis of ΔY.

The Cr1 and the Cb1 are multiplied by a enhancement parameter variable according to an absolute value of ΔY, in the first and second embodiments. However, only when ΔY is over a threshold value, may the Cr1 and the Cb1 be multiplied by a constant enhancement parameter.

The Cr1 and the Cb1 are enhanced on the basis of an absolute value of ΔY, in the first and second embodiments. However, the Cr1 and the Cb1 may be used for generating a video signal without enhancement. Without enhancement, the difference in fluorescence emission pattern may already be clearly displayed.

The influence of noise mixed into the pixel data of a focused pixel is reduced using the ΔY of the surrounding pixels, in the first and second embodiments. It is known that an area of tissue may autofluoresce differently from surrounding areas or have a luminance value lower than that of healthy tissue. Without noise reduction, it is still possible to generate an image in which said area is colored so as to be clearly distinguishable from other surrounding areas.

The chrominance difference data components are corrected so that the data level of the chrominance difference data component whose frequencies are the highest in the histogram of the chrominance difference data components approaches zero, in the first and second embodiments. However, the same effect as that of the first and second embodiments can be achieved if the chrominance difference data components are corrected such that a representative value calculated based on a plurality of chrominance difference data components, such as an average value of chrominance difference data components among the pixel data corresponding to the image, approaches zero.

The chrominance difference data components are corrected so that the data level of the chrominance difference data components whose frequency is the highest in the histogram of the chrominance difference data components approaches zero, in the first and second embodiments. However, the standard value to be matched by the data level of the chrominance difference data components whose frequency is the highest is not limited to zero. The same effect as that of the first and second embodiments can be achieved if the chrominance difference data components are corrected so that the data level of the chrominance difference data components whose frequency is the highest, matches a standard value which is near zero even if the standard value is not zero.

The coefficient (k), which is multiplied by the absolute value of $\Delta Y$ to calculate the enhancement parameter, can be changed based on a command input to the input block 23, in the first and second embodiments. However, the coefficient may be set to a constant value.

The chrominance difference data components are generated based on the red, green, and blue data components and the generated chrominance difference data components are corrected, in the first and second embodiments. However, the red, green, and blue data components can be directly corrected. The same effect as the first and second embodiments can be achieved if the red, green, and blue data components are corrected so that the data level of the chrominance difference data components whose frequency is the highest in the histogram of the chrominance difference data components corresponding to the corrected red, green, and blue data components, is made to approach zero.

The light-receiving surface of the imaging device 32 is covered with an RGB color filter, in the first and second embodiments. However, the light-receiving surface may be covered with an Mg-Cy-Ye-G complementary color filter. Based on magenta, cyan, yellow, and green data components, luminance and chrominance difference data components can be generated.

The laplacian or median filtering processing is carried out on the $\Delta Y$ of focused pixels, in the second embodiment. However, other filtering for noise reduction may also be carried out.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-133527 (filed on May 21, 2008), which is expressly incorporated herein, by reference, in its entirety.

The invention claimed is:

1. An endoscope processor, comprising:
a receiver that receives an image signal, the image signal corresponding to a captured subject, the image signal being generated by an imaging device, the image signal comprising a plurality of pixel signals corresponding to a plurality of pixels, the plurality of pixels forming an optical image of the subject; and
a correction circuit block that carries out first signal processing on the plurality of pixel signals so that a representative value matches a standard value when the image signal received by the receiver is a fluorescence image signal comprising the plurality of pixel signals, the representative value being calculated on the basis of a plurality of chrominance difference values corresponding to the plurality of pixel signals, the fluorescence image signal being generated when the subject is illuminated with excitation light, the excitation light making an organ fluoresce, wherein
the correction circuit block comprises a first generation circuit block, a first calculation circuit block, and a main correction circuit block,
the first generation circuit block generates chrominance difference signal components corresponding to the chrominance difference values on the basis of the pixel signal,
the first calculation circuit block calculates the representative value on the basis of the chrominance difference signal components corresponding to a plurality of the pixels of a single image signal, and
the main correction circuit block corrects the chrominance difference signal components of all the pixels so that the representative value matches the standard value.

2. An endoscope processor according to claim 1, wherein the representative value is a signal level of the chrominance difference signal component whose frequency is highest among a plurality of the chrominance difference values, or an average value of a plurality of the chrominance difference values.

3. An endoscope processor according to claim 1, wherein the color corresponding to a chrominance difference value that matches the standard value is an achromatic color.

4. An endoscope processor according to claim 2, further comprising:
a second generation circuit block that generates luminance signal components corresponding to the pixel signals on the basis of the pixel signals;
a second calculation circuit block that calculates luminance differences, the luminance differences being difference between first and second luminance values for the same pixel, the first luminance value corresponding to a luminance signal component based on a reference image signal, the reference image signal being generated when the subject is illuminated with reference light, a wavelength band of the reference light being broader than that of the excitation light, the second luminance value corresponding to a luminance signal component based on the fluorescence image signal; and
a color-enhancement circuit block that generates color-enhanced pixel signals by adjusting corrected pixel signals on the basis of the luminance differences, the corrected pixel signals being the pixel signals, on which the correction circuit block carries out first signal processing.

5. An endo scope processor according to claim 4,
wherein the color-enhancement circuit block adjusts the corrected pixel signals so that an adjusted difference is increased, the adjusted difference being a difference between the chrominance difference value corresponding to the corrected pixel signal and the standard value.

6. An endoscope processor according to claim 5,
wherein the color-enhancement circuit block increases the adjusted difference in proportion to the luminance difference.

7. An endoscope processor according to claim 6, further comprising:
an input apparatus to which a command for changing an increasing rate of the adjusted difference by the color-enhancement circuit block is input.

8. An endo scope processor according to claim 4,
wherein the color-enhancement circuit block finely adjusts the color-enhanced pixel signals using the luminance difference of surrounding pixel(s), the surrounding pixel(s) being a pixel(s) surrounding a focused pixel which is selected for focus, for the purpose of fine adjustment.

9. An endoscope processor according to claim 8,
wherein the color-enhancement circuit block finely adjusts the color-enhancement pixel signals by adjusting the corrected pixel signals on the basis of the luminance difference of the focused pixel having undergone one of differential filtering processing, laplacian filtering processing, and median filtering processing using the luminance difference of the surrounding pixel.

10. An endo scope processor according to claim 8,
wherein the color-enhancement circuit block finely adjusts the color-enhancement pixel signals according to a gap between an order in a luminance value of the focused pixel and a median order of luminance values among a group of the surrounding pixel(s) and the focused pixel.

11. An endoscope processor according to claim 7,
wherein the number of the surrounding pixel(s) for fine adjustment of the color-enhancement pixel signals can be changed.

12. An endoscope system, comprising:
an excitation-light source that supplies a subject with excitation light, the excitation light making an organ fluoresce;
an electronic endoscope that generates an image signal, the image signal corresponding to a captured subject, the image signal comprising a plurality of pixel signals corresponding to a plurality of pixels, the plurality of pixels forming an optical image of the subject; and
a correction circuit block that carries out first signal processing on the plurality of pixel signals so that a representative value matches a standard value when the image signal generated by the electronic endoscope is a fluorescence image signal comprising the plurality of image signals, the representative value being calculated on the basis of a plurality of chrominance difference values corresponding to the plurality of pixel signals, the fluorescence image signal being generated when the subject is illuminated with excitation light, wherein
the correction circuit block comprises a first generation circuit block, a first calculation circuit block, and a main correction circuit block,
the first generation circuit block generates chrominance difference signal components corresponding to the chrominance difference values on the basis of the pixel signal,
the first calculation circuit block calculates the representative value on the basis of the chrominance difference signal components corresponding to a plurality of the pixels of a single image signal, and
the main correction circuit block corrects the chrominance difference signal components of all the pixels so that the representative value matches the standard value.

* * * * *